United States Patent [19]

Ohno

[11] 4,331,403
[45] May 25, 1982

[54] PHOTOGRAPHING APPARATUS FOR ENDOSCOPE

[75] Inventor: Kunio Ohno, Tokyo, Japan

[73] Assignee: Olympus Optical Co., Ltd., Tokyo, Japan

[21] Appl. No.: 110,628

[22] Filed: Jan. 9, 1980

[30] Foreign Application Priority Data

Jan. 11, 1979 [JP] Japan .................................. 54-1987

[51] Int. Cl.$^3$ ............................................. G03B 29/00
[52] U.S. Cl. .................................... 354/62; 128/634; 339/278 A
[58] Field of Search ................. 354/62; 128/634, 6–9; 339/278 A

[56] References Cited

U.S. PATENT DOCUMENTS 4,223,313 6/1980 Chabrol ........................ 340/870.07

FOREIGN PATENT DOCUMENTS 53-38322 4/1978 Japan .

Primary Examiner—Russell E. Adams

[57] ABSTRACT

An electrostatic coupling means is provided between a camera and an eyepiece section of an endoscope, and a second electrostatic coupling means is provided between a connector section of said endoscope and a light source unit. A high frequency signal of a high frequency generator provided in the camera is received by a receiving circuit in the light source unit through the electrostatic coupling means, and control of the light emission of the light source is made on the basis of the received signal.

4 Claims, 6 Drawing Figures

FIG. 3
FIG. 4
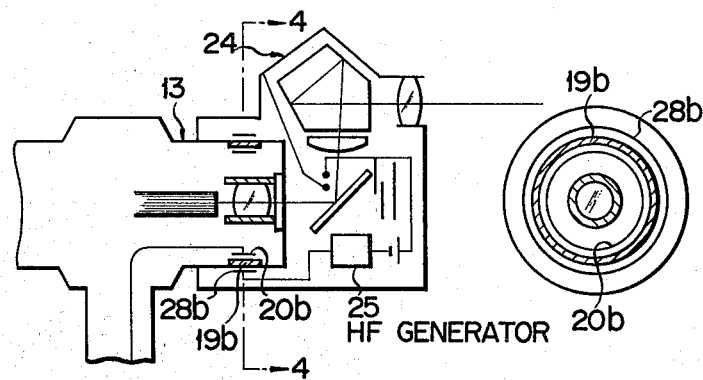
FIG. 5
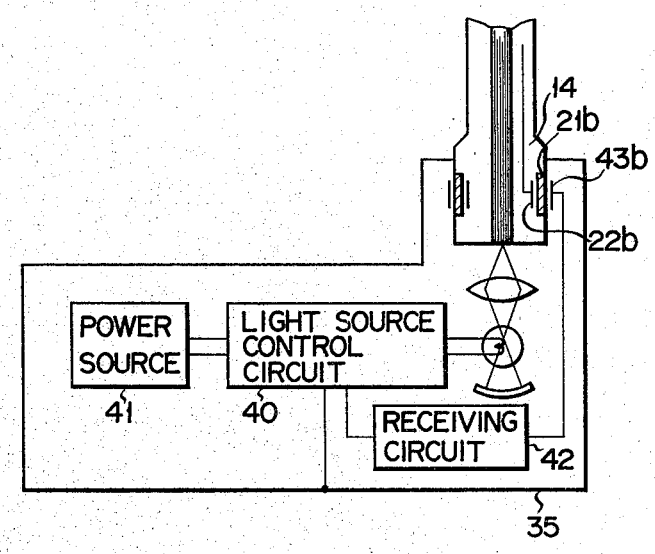

PHOTOGRAPHING APPARATUS FOR ENDOSCOPE

BACKGROUND OF THE INVENTION

This invention relates to a photographing apparatus for an endoscope.

In the prior art photographing apparatus for endoscopes, a camera which is mounted on an eyepiece section of the endoscope and a light source device which is coupled to a connector section of the endoscope are electrically connected to each other through switches or contacts provided in the endoscope for the purpose of causing light emission of the light source unit in response to the camera shutter release action and also controlling the quantity of light emitted from the light source device. With the construction using contacts for connecting the camera and light source device, however, contact failure due to such cause as corrosion and oxidation of the contacts is likely to occur, and in such a case satisfactory photographing cannot be obtained.

SUMMARY OF THE INVENTION

An object of the invention is to provide a photographing apparatus for an endoscope, which has resort not to connection through contacts but to electrostatic induction for coupling together the camera, endoscope and light source device.

The invention features a photographing apparatus for an endoscope, which comprises an electrostatic coupling means provided between the endoscope and a camera mounted on an eyepiece section of the endoscope and a second electrostatic coupling means provided between the endoscope and a light source unit connected to the endoscope, and in which a high frequency signal from a high frequency generator provided at least either in the camera or in the light source unit is coupled through the electrostatic coupling means for controlling the photographing.

BRIEF DESCRIPTION OF THE DRAWINGS

FIG. 3 is a schematic diagram showing a camera and an eyepiece section of an endoscope in a further embodiment of the photographing apparatus employing ring-like electrostatic coupling means;

FIG. 4 is a section taken along line 4—4 in FIG. 3;

FIG. 5 is a schematic diagram showing a connector section of the endoscope and a light source unit in the embodiment of FIG. 3 having the ring-like electrostatic coupling means.

DETAILED DESCRIPTION OF THE PREFERRED EMBODIMENTS

Figure 1:
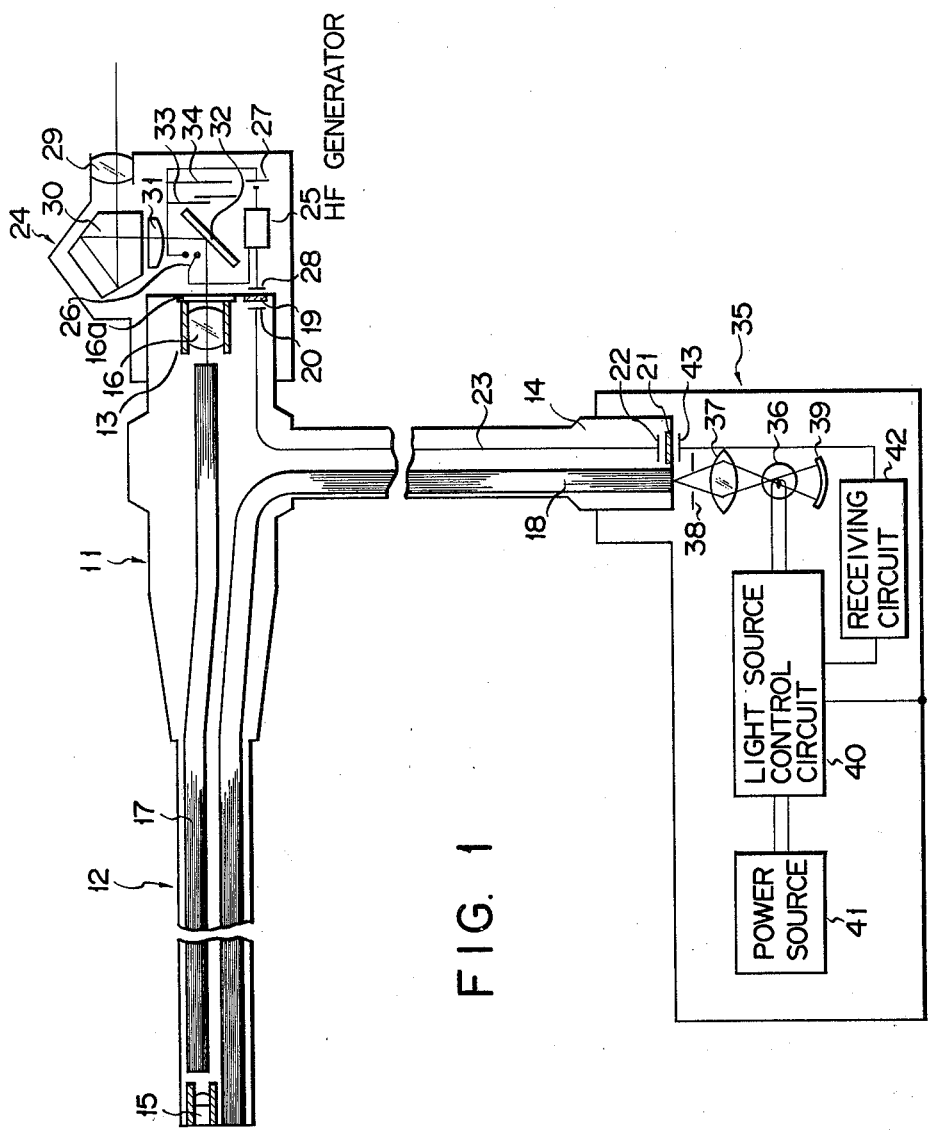
FIG. 1 is a schematic diagram showing an embodiment of the photographing apparatus for an endoscope according to the invention.

Referring now to FIG. 1, an endoscope 11 has an insertion section 12, an eyepiece section 13 and a connector section 14. The insertion section 12 is provided at the tip thereof with an objective 15, and the eyepiece section 13 is provided with an eyepiece 16 of the endoscope. An image guide 17 formed of, for example, optical fibers extends from the objective 15 to the eyepiece 16 of the endoscope. Also, a light guide 18 formed of, for example, optical fibers extends from the tip of the objective section 12 to the tip of the connector section 14. A protective glass 16a is provided between the eyepiece 16 of the endoscope and the end face of the eyepiece 16 of the endoscope. The eyepiece section 13 is provided at the end face thereof with a dielectric member 19, and inside the endoscope an electrode plate 20 is provided in the close proximity of and to face the dielectric member 19. The connector section 14 is also provided at the end face thereof with a dielectric member 21, and an electrode plate 22 is provided in the close proximity of and to face the dielectric member 21. The electric plates 20 and 22 are electrically connected together by a conductor 23.

A camera 24, which is mounted on the eyepiece section 13 of the endoscope 11, is provided with a high frequency generator 25. A power supply 27 is connected through a mirror switch 26 to a power input terminal of the high frequency generator 25. A high frequency output terminal of the high frequency generator 25 is connected to an electrode plate 28. The electrode plate 28 is provided inside the camera 24 such that it faces the electrode plate 20 provided in the eyepiece section 13 of the endoscope 11. The electrode plate 28 of the camera is preferably in the close proximity of the dielectric member 19 in the eyepiece section 13. Like the usual camera, the camera 24 is provided with a camera eyepiece 29, a pentaprism 30, a condenser 31, a mirror 32 and a shutter 33. A film 34 is provided behind the shutter 33.

In a light source unit 35, which is connected to the connector section 14 of the endoscope 11, a light source 36 is disposed such as to face the tip of the light guide 18 of the endoscope 11 via a condenser 37 and a diaphragm 38. A concave mirror 39 is provided on the side of the light source opposite the condenser 37. The light source 36 is connected to a light source control circuit 40. The light source control circuit 40 is furnished with power from a power source 41. The light source control circuit 40 has a control input terminal connected through a receiving circuit 42 to an electrode plate 43, which is provided in the close proximity of and to face the dielectric member 21 provided in the connector section 14.

In the photographing apparatus for endoscope of the above construction, the electrode plate 20 of the endoscope and the electrode plate 28 of the camera form a capacitor, and also the electrode plate 22 of the endoscope and the electrode plate 43 of the light source unit 35 form a capacitor. In other words, the high frequency generator 25 of the camera 24 and the receiving circuit 42 of the light source unit 35 are electrostatically coupled together through these capacitors. When a shutter release button (not shown) of the camera is depressed, the mirror 32 is raised, and with this movement of the mirror switch 26 is closed. As a result, the high frequency generator 25 is energized by the power source 27 and produces a high frequency signal. The high frequency signal thus produced is coupled to the conductor 23 of the endoscope 11 through the capacitor formed by the electrode plates 20 and 28. The high frequency signal coupled to the conductor 23 is supplied to the high frequency receiving circuit 42 through the capacitor formed by the electrode plates 22 and 43. In response to the reception of the high frequency signal the high frequency receiving circuit 42 supplies an output signal to the light source control circuit 40, so that the power of the power source 41 is supplied to the light source 36 through the control circuit 40. As a result, the light source 36 is caused to emit light which is gathered through the condenser 37 to be directed through the diaphragm 38 to the end of the light guide 18. The light thus transmitted to the light guide 18 is led therethrough and projected to the outside, that is, to a cavity wall of the human body. Light reflected from the cavity wall of the body is transmitted through the objective 15, image guide 17, endoscope eyepiece 16, protective glass 16a and shutter 33 in the mentioned order to reach the film 34, whereby the film 34 is exposed.

As has been shown, according to the invention the high frequency generator 25 of the camera and high frequency receiving circuit 42 of the light source unit 35 is electrostatically coupled together through the capacitor formed by the electrode plate 20 of the endoscope and the electrode plate 28 of the camera and the capacitor formed by another electrode plate 22 of the endoscope and an electrode plate 43 of the light source unit, so that the possibility of contact failure as in the prior art can be eliminated. In addition, since the electrode plates need not be revealed, their corrosion and oxidation due to antiseptic liquid is not likely. While in the above embodiment the light source is controlled in response to the transmitted high frequency signal, the same effects may also be obtained with such an arrangement as to control the diaphragm aperture. Further, while the high frequency generator of the camera is adapted to respond to the action of the mirror switch, it may as well have a construction responsible to the action of a shutter mechanism such as the shutter release button or shutter itself.

Figure 2:
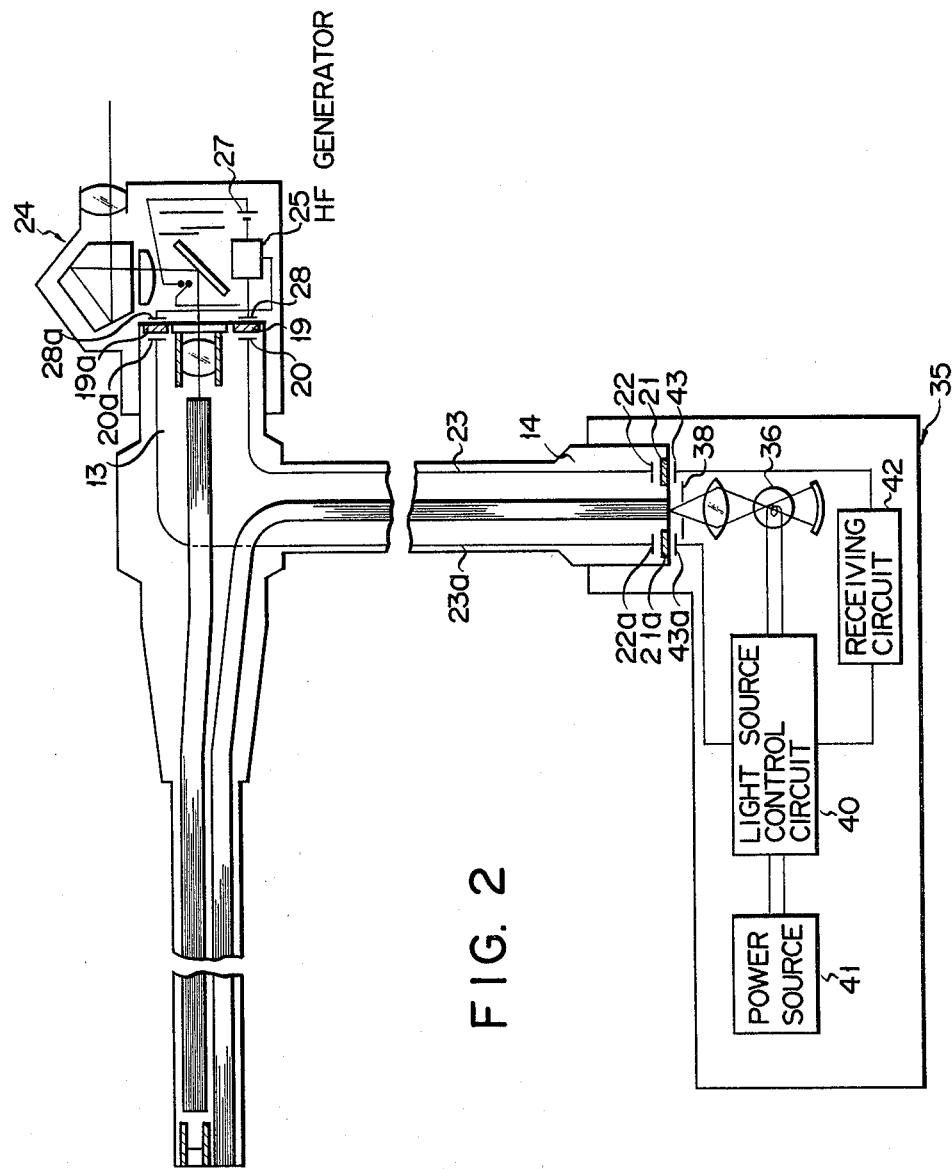
FIG. 2 is a schematic diagram showing another embodiment of the photographing apparatus for an endoscope, in which electrostatic coupling means are provided both in the forward and return paths of a closed loop formed with the camera, endoscope and light source unit.

A second embodiment will now be described with reference to FIG. 2. Like parts as those in the preceding embodiment of FIG. 1 are designated by like reference symbols and not described any further. While in the embodiment of FIG. 1 the closed loop is formed through the conductive bodies of the camera, endoscope and light source unit and capacitors formed by the electrode plates, in the embodiment of FIG. 2 the closed loop is formed without making use of the bodies of the camera, endoscope and light source unit. More particularly, the eyepiece section 13 of the endoscope is provided with another electrode plate 20a and another dielectric member 19a, and the connector section 14 is provided with another electrode plate 22a and another dielectric member 21a. The electric plates 20a and 22a are connected together by a conductor 23a. The camera is also provided with another electric plate 28a, which is connected to another output terminal of the high frequency generator 25. Further, the light source unit 35 is provided with another electrode plate 43a, which is connected to another input terminal of the receiving circuit 42 and light source control circuit 40. In this embodiment, the electrode plates 19a and 20a form a capacitor, while the electrode plates 22a and 43a form a capacitor, with the closed circuit being formed through these capacitors.

FIGS. 3 and 4 show a further embodiment, in which a dielectric member 19b in the form of a ring is provided to surround the endoscope eyepiece 13 together with a coaxial ring-like electrode plate 20b disposed in the close proximity of and to face the inner side of the ring-like dielectric member 19b. On the side of the camera, a ring-like dielectric member 28b is coaxially disposed in the close proximity of and to face the outer side of the ring-like dielectric member 19b of the endoscope. Further, as shown in FIG. 5 in the connector section 14 of the endoscope an outer ring-like dielectric member 21b and an inner ring-like electrode plate 22b are coaxially provided in the close proximity of and to face each other. On the side of the light source unit 35 a coaxial ring-like electrode plate 43 is provided in the close proximity of and to face the ring-like dielectric member 21b. With the construction of the electrode plates as shown in FIGS. 3 to 5 the electrostatic capacitance between the pair electrode plates is increased to permit more reliable action to be expected. The electrode plates and dielectrics may cover the entire length of or a part of the periphery or an end portion of the engagement section between the eyepiece section of the endoscope and camera and the engagement section between the connector section of the endoscope and light source unit.

Figure 6:
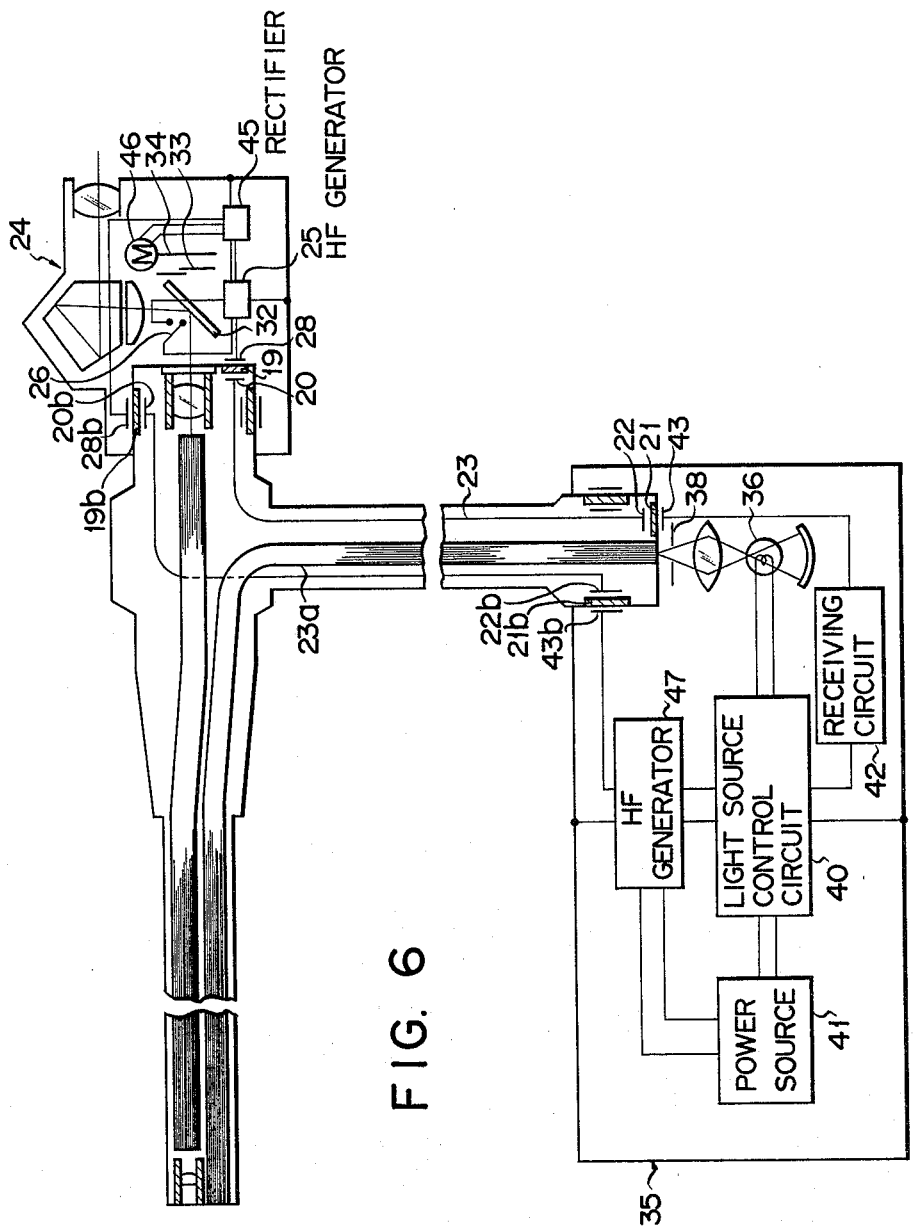
FIG. 6 is a schematic diagram showing a still further embodiment of the photographing apparatus for an endoscope according to the invention.

FIG. 6 shows a further embodiment, in which the eyepiece section 13 of the endoscope is provided at the end face with a dielectric member 19 and an electrode plate 20 and over the periphery with a ring-like dielectric member 19b and an electrode plate 20b. Similarly, the connector section 14 is provided at the end face with a dielectric member 21 and an electrode plate 22 and over the periphery with a ring-like dielectric member 21b and a ring-like electrode plate 22b. For the camera 24 an end face electrode plate 28 and a ring-like electrode plate 28b are provided. The ring-like electrode plate 28b is connected to a high frequency rectifier (e.g. AC-DC converter) 45 which is provided in the camera 24. The high frequency rectifier 45 has output terminals connected to power input terminals of a film take-up motor 46 and those of a high frequency generator 25. For the light source unit 35 an end face electrode plate 43 and a ring-like electrode plate 43b are provided. The ring-like electrode plate 43b is connected to one of the output terminals of a high frequency generator 47. The high frequency generator 47 is controlled by a light source control circuit 40 which is furnished with power from a power source circuit 41. In this embodiment of FIG. 6, the high frequency current from the high frequency generator 47 in the light source unit 35 is supplied through a capacitor constituted by the ring-like electrode plates 43b and 22b, a conductor 23a and a capacitor constituted by the ring-like electrode plates 20b and 28b to the high frequency rectifier 45 of the camera. The rectified output of the rectifier 45 is used as power for driving the high frequency generator 25 and film take-up motor 46. The other operations in the instant embodiment are the same as in the previous embodiment of FIG. 1, so that they are not described here. The power supply provided in the camera may also be coupled to an amplifier, which amplifies an output signal of a light receiving device measuring the quantity of light led through the image guide for automatic exposure control.

As has been described in the foregoing, according to the invention electrostatic and contact-free coupling of the camera and light source unit can be obtained by the provision of electrode plates in the camera, endoscope and light source unit. Thus, the electric system of the apparatus is not adversely affected at all from sterilization of the endoscope by immersing it in an antiseptic liquid.

What is claimed is:

1. A photographing apparatus for an endoscope comprising an endoscope including an eyepiece section and a connector section, a camera mounted on said eyepiece section of said endoscope, a light source unit connected to said connector section of said endoscope and including a light source, a first electrostatic coupling means provided between said eyepiece section and said camera, and comprising a first dielectric member provided on said eyepiece section, a first electrode plate facing said first dielectric member and a second electrode plate provided on said camera and facing said first dielectric member, a second electrostatic coupling means provided between said connector section of said endoscope and said light source unit, a second dielectric member provided on said connector section, a third electrode plate facing said dielectric member and a fourth electrode plate provided on said light source unit and facing said second dielectric member, a high frequency generator provided in said camera and connected to said second electrode plate, said high frequency generator producing a high frequency signal, at least one connecting member connecting together said first and second electrostatic coupling means, a high frequency receiving circuit provided in said light source unit and connected to said second electrostatic coupling means, and means for controlling the light emission of said light source in response to the output of said receiving circuit.

2. A photographing apparatus for an endoscope according to claim 1, wherein said first electrostatic coupling means includes a first ring-like electrode plate disposed on said camera, a second ring-like electrode plate disposed on said eyepiece section and in the close proximity of and to face said ring-like first electrode plate and a ring-like dielectric member interposed between said first and second electrode plates.

3. A photographing apparatus for an endoscope according to claim 1 or 2, wherein said second electrostatic coupling means includes a first ring-like electrode plate disposed on said connector section of said endoscope, a second ring-like electrode plate disposed on said light source unit and in the close proximity of and to face said first ring-like electrode plate and a ring-like dielectric member interposed between said first and second electrode plates.

4. A photographing apparatus for an endoscope according to claim 1, wherein said light source unit further includes a high frequency generator for producing high frequency energy, and also wherein said camera includes a high frequency rectifier, said high frequency rectifier serving to rectify the high frequency energy from said high frequency generator in said light source unit and producing a rectified output to said high frequency generator provided in said camera.

* * * * *